(12) United States Patent
Shameem et al.

(10) Patent No.: US 7,632,491 B2
(45) Date of Patent: Dec. 15, 2009

(54) STABLE PEGYLATED INTERFERON FORMULATION

(75) Inventors: Mohammed Shameem, Nanuet, NY (US); Anita Dabbara, Princeton Junction, NJ (US)

(73) Assignee: Schering Corporation, Kenilworth, NJ (US)

( * ) Notice: Subject to any disclaimer, the term of this patent is extended or adjusted under 35 U.S.C. 154(b) by 501 days.

(21) Appl. No.: 11/201,731

(22) Filed: Aug. 11, 2005

(65) Prior Publication Data

US 2006/0051320 A1 Mar. 9, 2006

Related U.S. Application Data

(60) Provisional application No. 60/600,846, filed on Aug. 12, 2004.

(51) Int. Cl.
*A61K 38/19* (2006.01)
*A61K 38/21* (2006.01)
*A61K 38/00* (2006.01)

(52) U.S. Cl. .................... 424/85.4; 424/85.1; 424/85.7; 514/12; 530/350; 530/351

(58) Field of Classification Search ........................ None
See application file for complete search history.

(56) References Cited

U.S. PATENT DOCUMENTS

| | | | |
|---|---|---|---|
| 4,496,537 A | 1/1985 | Kwan | |
| 5,595,732 A | 1/1997 | Hakini et al. | |
| 5,691,298 A | 11/1997 | Gosselink et al. | |
| 5,762,923 A | 6/1998 | Gross et al. | |
| 5,951,974 A | 9/1999 | Gilbert et al. | |
| 6,180,096 B1 | 1/2001 | Kline | |

FOREIGN PATENT DOCUMENTS

| | | |
|---|---|---|
| EP | 0 420 049 | 4/1991 |
| EP | 0 593 868 | 4/1994 |
| EP | 0 736 303 | 9/1996 |
| EP | 0 809 996 | 3/1997 |
| WO | WO 95/13090 | 5/1995 |
| WO | WO 96/11018 | 4/1996 |
| WO | WO 96/24369 | 8/1996 |
| WO | WO 97/18832 | 5/1997 |
| WO | WO 98/48840 | 11/1998 |
| WO | WO 01/12214 A | 2/2001 |
| WO | WO 03/049760 A | 6/2003 |

OTHER PUBLICATIONS

Carpenter, J. F. et al., "Rational Design of Stable Lyophilized Protein Formulations: Some Practical Advice" *Pharmaceutical Research*, 14(8):969-975 (1997).
Carpenter, J. F. et al., "Rational Design of Stable Lyophilized Protein Formulations: Theory and Practice" *Rational Design of Stable Protein Formulations*, J. F. Carpenter and M. C. Manning Editors, pp. 109-133, Kluwer Academic / Plenum Publishers, New York (2002).
Chang, B. S. et al., "Physical Factors Affecting the Storage Stability of Freeze-Dried Interleukin-1 Receptor Antagonist: Glass Transition and Protein Conformation", *Archives of Biochemistry and Biophysics*, 331(2):249-258 (1996).
Fox, Karen Celia, "Putting Proteins Under Glass", *Science*, 267:1922-1923 (Mar. 31, 1995).
Heller, M. C. et al., "Conformational Stability of Lyophilized PEGylated Proteins in a Phase-Separating System," *Journal of Pharmaceutical Sciences*, 88(1):58-64 (1999).
The Merck Index, 12th ed. Merck & Co., Inc., Whitehouse Station, N.J., pp. 1517-1518, entry No. 9051, 1996.
PEG-Intron® Product Information, Rev. 2/05.
Tang, X. (C) et al., "Design of Freeze-Drying Process of Pharmaceuticals: Practical Advice", *Pharmaceutical Research*, 21(2):191-200 (Feb. 2004).
International Search Report for related International Application No. PCT/US2005/028441, mailed Apr. 13, 2006 (5 pages).
Written Opinion of the International Searching Authority for related International Application No. PCT/US2005/028441, mailed Apr. 13, 2006 (7 pages).

*Primary Examiner*—Christine J Saoud
*Assistant Examiner*—Jegatheesan Seharaseyon

(57) ABSTRACT

The present invention relates to lyophilized formulations of pegylated interferon which are prepared using trehalose as a cryoprotectant. The formulations have a low moisture content, which helps stabilize the pegylated interferon during storage of the formulations at room temperature. In addition, methods for preparing these formulations are provided.

36 Claims, No Drawings

STABLE PEGYLATED INTERFERON FORMULATION

RELATED APPLICATIONS

This application claims the benefit of U.S. provisional application Ser. No. 60/600,846 filed Aug. 12, 2004.

FIELD OF THE INVENTION

The present invention relates to stable formulations of pegylated-interferon conjugates, which are useful for treating a variety of conditions for which interferon therapy is beneficial. In particular, formulations are provided that include the active pharmaceutical ingredient pegylated interferon and trehalose, which are stable at room temperature when lyophilized.

BACKGROUND OF THE INVENTION

Interferons are a family of highly homologous proteins that inhibit viral replication, inhibit cellular proliferation and modulate immune response. Human interferons are grouped into three classes based on their cellular origin and antigenicity: α-interferon (leukocytes), β-interferon (fibroblasts) and γ-interferon (B cells). Recombinant forms of each group have been developed and are commercially available.

Due to their various biological activities, the use of interferons for treating a number of conditions has been proposed, including viral infections and various cancers. However, as with other proteins, use of interferons as pharmaceutical agents has generally been limited by several shortcomings, including antigenicity, which leads to formation of neutralizing antibodies and loss of clinical response, and a short half-life, which means that frequent doses are required to maintain therapeutically-effective concentrations of the protein.

These problems can be overcome by conjugating interferon to polymers, such as polyethylene glycol. However, while interferon-polymer conjugates are clinically beneficial, the widespread use of such conjugates in clinical practice requires formulations that can be stored for an extended period of time during manufacture and distribution to health care providers. Some interferon-polymer conjugates, however, rapidly deteriorate, even in frozen solutions. Lyophilization (also known as freeze-drying) is a process that can render an interferon-polymer conjugate in a form that can overcome this deficiency.

Lyophilization is a process whereby water is sublimed from a composition after it is frozen. In this process, pharmaceuticals and biologicals that are relatively unstable in an aqueous solution over a period of time can be placed into dosage containers in an easily processed liquid state, dried without the use of damaging heat and stored in a dried state for extended periods. A formulation designed for lyophilization often contains bulking ingredients that increase the amount of solid material, as well as cryoprotectants, lyoprotectants and other stabilizers to protect the active ingredient from damage during and after lyophilization.

U.S. Pat. No. 6,180,096 discloses that lyophilization of pegylated-interferon alpha conjugates may result in changes in the nature and degree of conjugation of PEG to interferon α. Such changes include degradation of the conjugate into free PEG and interferon α, subsequent attachment of the free PEG onto another pegylated-interferon molecule, or intramolecular shifts of PEG molecules from one site of conjugation to another within the same molecule. This patent discloses that the stability of pegylated-interferon alpha conjugates during and after lyophilization is achieved by lyophilizing such conjugates in a buffer, a stabilizer, a cryoprotectant and a solvent. While the '096 patent mentions several cryoprotectants could be used, including disaccharides, sucrose is the only cryoprotectant used in the only formulation that is specifically exemplified in this patent.

Lyophilized formulations containing Peginterferon alpha-2b, dibasic sodium phosphate anhydrous, monobasic sodium phosphate dihydrate, sucrose and polysorbate 80 are marketed by Schering Corporation, Kenilworth, N.J. as PEGINTRON™ vials and the PEGINTRON™ REDIPEN®(Single-dose Delivery System) (See PEGINTRON™ Product Information, Rev. 2/05.). The REDIPEN® Single-dose Delivery System is a dual-chamber glass cartridge containing lyophilized peginterferon alfa-2b in one chamber and sterile water for injection in the other chamber. The manufacturer recommends room-temperature storage for PEGINTNTRON™ vials (i.e., 25° C.), and refrigerated storage for PEGINTRON™ REDIPEN® cartridges (i.e., 2° to 80° C.).

There is a present need for additional formulations that not only protect pegylated interferon conjugates from damage during and after lyophilization, but that also allow long-term storage at room temperature when lyophilized in glass cartridges. Ideally, such formulations should be amenable to a manufacturing process that is more cost-effective than the process used for sucrose-based formulations.

SUMMARY OF THE INVENTION

The present invention is based on the surprising discovery that the use of trehalose, as the sole cryoprotectant or in combination with other cryoprotectants, during lyophilization of pegylated interferon alpha 2b allows use of significantly shorter lyophilization cycles while producing a lyophilized powder that is lower in moisture content and thus more stable at room temperature than when sucrose is used as the sole cryoprotectant. Reducing the moisture content has been found to significantly increase the room temperature stability of certain pegylated interferons in a lyophilized formulation.

These beneficial effects of trehalose were unexpected because the collapse temperature (Tc) and glass transition temperature (Tg') of a frozen pegylated interferon solution with trehalose as the only cryoprotectant (−29.5° C. and −27° C., respectively) are not much higher than the Tc and Tg' of the same solution when sucrose is used instead of trehalose as the only cryoprotectant (−32.7° C. and −32° C., respectively). In theory, the primary drying step in lyophilizing a pegylated interferon formulation should be performed well below the Tc and Tg'; otherwise the cake may collapse due to warming of the product, which may cause the cake to contain higher moisture content, which can lead to reduced stability of the pegylated interferon. Thus, the skilled artisan seeking to reduce the moisture content of sucrose-based pegylated interferon formulations in glass cartridges would not have considered using a cryoprotectant with a higher Tc or Tg' than that of sucrose. However, as described in more detail below, the inventors herein surprisingly discovered that the use of trehalose as a cryoprotectant allows the primary drying step to be performed at temperatures higher than the Tc and Tg' of the frozen solution, while achieving a lyophilized product that has both low moisture content and minimal cake defects.

Thus, the formulations of the invention comprise a pegylated interferon as the active pharmaceutical ingredient and trehalose as a cryoprotectant. The formulations of the invention may contain one or more other agents that perform a cryoprotectant function, provided that trehalose comprises at least 60%, by weight, of all such agents that are present. The presence of trehalose during lyophilization of pegylated interferons in dual chamber glass cartridges has been found to allow use of a relative short lyophilization cycle (e.g., <3 days versus >5 days for the same formulation containing sucrose as the sole cryoprotectant) to produce a lyophilized powder of low initial moisture content and low hygroscopicity, with minimal rejects due to cake collapse, shrunkenness, liddedness or meltback.

In one embodiment, the present invention provides a solution for preparing a lyophilized powder formulation. The solution comprises a pegylated interferon, a cryoprotectant, a buffer, a stabilizer, and Sterile Water for Injection, wherein trehalose comprises at least 60%, by weight, of the cryoprotectant.

Another specific embodiment of the invention is a lyophilized powder comprising a pegylated interferon, a cryoprotectant, a buffer, and a stabilizer, wherein trehalose comprises at least 60%, by weight, of the cryoprotectant and the lyophilized powder has a moisture content less than 3%.

Yet another embodiment of the invention is a pegylated-interferon drug product, which comprises a glass container, which comprises a lyophilized powder comprising a pegylated interferon, a cryoprotectant, a buffer, and a stabilizer, wherein trehalose comprises at least 60%, by weight, of the cryoprotectant and the powder has a moisture content less than 3%. In a preferred embodiment the glass container is a cartridge having first and second chambers, wherein the first chamber contains the lyophilized powder and the second chamber contains Sterile Water for Injection, which is used for reconstituting the powder into a solution for injection.

In addition, the present invention provides methods for preparing lyophilized pegylated interferon formulations. Such methods comprise lyophilizing a pegylated interferon in the presence of a cryoprotectant, a buffer, a stabilizer, and Sterile Water for Injection, wherein trehalose comprises at least 60%, by weight, of the cryoprotectant. The lyophilization is performed under conditions that produce a moisture content less than 3%.

DETAILED DESCRIPTION OF THE INVENTION

The present invention provides novel lyophilized formulations of pegylated interferons that are stable during long-term storage at room temperature, as well as processes for preparing these formulations. This section presents a detailed description of these formulations, their preparation and their applications. This description is by way of several exemplary illustrations, in increasing detail and specificity, of the various embodiments of this invention. These examples are non-limiting, and related variants that will be apparent to one of skill in the art are intended to be encompassed by the appended claims.

So that the invention may be more readily understood, certain technical and scientific terms are specifically defined in this section. All other technical and scientific terms used herein have the meaning commonly understood by one of ordinary skill in the art to which this invention belongs.

As used herein the term "pegylated interferon" means covalent conjugates of one or more polyethylene glycol (PEG) molecules and one or more interferon molecules. Preferred conjugates for use in the formulations of the invention have one to four PEG molecules per interferon molecule, and more preferably, the conjugates are between a single PEG molecule and a single interferon molecule. The pegylated interferon may comprise a single positional isomer or a mixture of conjugate positional isomers, e.g., the PEG molecules are covalently attached to different amino acid residues on the individual interferon molecules. For example, U.S. Pat. No. 5,951,974 describes the preparation of mixtures of PEG-interferon alpha conjugate positional isomers in which some of the isomers are conjugates between PEG and a histidine residue of the interferon molecule, other isomers in the mixture are conjugates between PEG and an interferon lysine residue and still other isomers are conjugates between PEG and the amino terminus of the interferon molecule. Preferably, the pegylated interferon component of the formulations of the invention comprises a mixture of positional isomers in which at least 15%, and more preferably at least 30%, of the conjugates in the mixture are between a single PEG molecule and a single interferon molecule at a histidine residue.

The PEG molecules in the conjugates may have different molecular weights. Preferably, the PEG molecules have an average molecular weight ranging between 1,000 and 15,000. In a particularly preferred embodiment, the conjugates are prepared using $PEG_{12000}$, i.e., which means the PEG molecules in the conjugates will have an average molecular weight of about 12,000.

The interferon portion of the pegylated interferon conjugates used in the present invention may be any naturally-occurring or recombinant interferon known to those skilled in the art. Natural and recombinant α-interferons that may be used in the formulations of the invention include interferon α-n1 (e.g., SUMIFERON®, Sumitomo Pharmaceuticals, Co., Ltd.), interferon α-n3, interferon α-2a (ROFERON®-A, Hoffmann-LaRoche, Inc.) interferon α-2b (INTRON® A, Schering-Plough Corp.), interferon α-2c (BEROFOR®, Boehringer Ingelheim, Inc.), and consensus interferon (INFERGEN®, InterMune, Inc.). β-interferons and γ-interferons that are suitable for practicing the invention include interferon β-1 a (AVONEX®, Biogen Idec), interferon β- 1b (BETASERON®, Berlex Laboratories, Richmond, Calif.) and interferon γ-1b (ACTIMMUNE®, InterMune, Inc.). Preferred interferons are interferon α-2a and interferon α-2b. Most preferably, interferon α-2b is used to prepare the active ingredient of the formulations of the present invention.

Conjugation of the PEG and interferon molecules may be performed by any conjugation reaction known to those skilled in the art, e.g., as described in U.S. Pat. Nos. 5,612,460, 5,711,944 and 5,951,974. Preferably, the PEG molecule is covalently attached to the interferon molecule with a urethane bond. More preferably, the pegylated interferon is generated by reacting interferon with methoxypoly(ethylene glycol)-succinimidyl carbonate (SC-PEG) at pH 6.5, as described in U.S. Pat. No. 5,951,974.

The most preferred pegylated interferon for use in the formulations of the invention is $PEG_{12000}$-interferon α-2b.

In addition to a pegylated interferon, the formulations of the present invention comprise a cryoprotectant, which protects the pegylated interferon from damage, adsorption and loss from vacuum utilized in lyophilization. The cryoprotectant also serves to stabilize the pegylated interferon during the freeze-drying process and in the resulting lyophilized powder, and as a bulking agent to form an easily reconstitutible cake. The amount of cryoprotectant used is typically based on the total weight of the formulation. In one embodiment, the cryoprotectant is present in an amount of 0.05% to 90% of the total weight. In preferred embodiments, the formulation comprises an amount of cryoprotectant that is between 0.05% and 50%, and more preferably between 0.15% and 10%, of the total weight of the formulation.

Trehalose comprises at least 60% of the total weight of the cryoprotectant in the formulation. The cryoprotectant may comprise trehalose in any percentage between 60% and 100% by weight, e.g., 65%, 70%, 75%, 80%, 85%, 90%, 95% or 100%. Preferably, trehalose comprises at least 75% of the total weight of cryoprotectant. More preferably, at least 80% of the cryoprotectant, by weight, is trehalose and most preferably, trehalose constitutes 100% of the cryoprotectant.

Trehalose is a disaccharide containing two glucose molecules bound in an α,α-1,1 linkage. Any form of trehalose is suitable for use in preparing the formulations of the present invention. A preferred form of trehalose is trehalose, dihydrate.

Other agents that may be used with trehalose in the cryoprotectant are carbohydrates such as the saccharides, sucrose, sugar alcohols such as mannitol, surface active agents such as the Tweens, as well as glycerol and dimethylsulfoxide. A preferred cryoprotectant is a carbohydrate. A preferred carbohydrate is a disaccharide. A preferred disaccharide is sucrose.

In one preferred embodiment, the formulations are prepared by lyophilizing a solution containing 60 mg/ml trehalose dihydrate and 40 mg/ml sucrose as the cryoprotectant. In a more preferred embodiment, the solution comprises 80 mg/ml trehalose dihydrate and 20 mg/ml sucrose as the cryoprotectant. In a yet more preferred embodiment, the cryoprotectant consists of trehalose dehydrate, which is present in the solution at 90 mg/ml trehalose.

The formulations of the invention also contain a buffer for maintaining the pH of the formulation in a range of 4.5 to 7.1. Preferably, the buffer maintains the pH between 6.5 and 7.1 and most preferably maintains the pH at 6.8. A preferred buffer comprises equal mass amounts of sodium phosphate dibasic anhydrous and sodium phosphate monobasic monohydrate, with the total concentration of these compounds in the formulation being between 0.005 and 0.1 molar. Other suitable buffer systems to maintain the desired pH range include sodium citrate/citric acid and sodium acetate/acetic acid.

The formulations of the present invention also contain a stabilizer for preventing adsorption of the pegylated-interferon to the stainless steel and glass surfaces of the equipment and containers used to lyophilize and store the formulations. In addition, stabilizers can stabilize the pegylated interferon by minimizing its exposure to air-water and ice-water interfaces during lyophilization and storage. As one example, polysorbates are useful as stabilizing agents. Polysorbate 80 is a preferred stabilizing agent. When polysorbate 80 is utilized, the preferred concentration is 0.01 to 1 mg/ml. Other suitable stabilizers are surface active agents such as polyvinyl alcohol (PVA) and PEG 300, which may be used at <2% of the volume of the solution used for the lyophilized formulation.

To prepare the formulations of the present invention, the pegylated interferon, cryoprotectant, buffer and stabilizer are dissolved in Water for Injection in an amount selected to achieve concentrations of the solid ingredients that are suitable for lyophilization. As used herein, the term "Water for Injection" means sterile, purified water that meets regulatory standards for particulates, dissolved solids, organics, inorganics, microbial and endotoxin contaminants.

Once all the formulation ingredients are in solution, the solution is aliquoted into glass containers suitable for use in a lyophilizer and for storage of the resulting lyophilized powder. Preferred containers are vials and cartridges. As used herein, the term "vial" refers to a small glass container with a flat or slightly concaved bottom, short neck and flat flange designed for stoppering. Vials are usually placed directly on the lyophilizer chamber trays or shelves for direct heat transfer. As used herein, the terms "cartridge" and "dual chamber cartridge" are used interchangeably to refer to a tube-like glass container having two chambers that are separated by a middle stopper. One chamber (Active Chamber) has a narrow neck and is closed by a snap-on closure. The other chamber (Diluent Chamber) is wider and closed by an end stopper. Cartridges are usually placed on magazines, which hold the cartridges upright, and then the magazines are placed directly on the lyophilizer trays/shelves. The cartridges may or may not be in direct contact with the lyophilizer tray/shelf surfaces for heat transfer.

Glass containers containing a pegylated interferon formulation of the invention are subjected to lyophilization under conditions appropriate to produce a lyophilized powder having a moisture content of less than 3%. Preferably, the lyophilized powder has a moisture content of between 0.5% and 2.5%, and more preferably between 1% and 2%.

The lyophilization conditions are also chosen to achieve acceptable levels of cake defects while maintaining the desired low moisture content. As used herein, the phrase "cake defect" refers to a cake that has one or more physical defects, such as collapse, shrinkage, liddedness, or meltback. Collapsed cakes, which are usually due to excessive warming of the formulation during freeze-drying, are associated with loss of product elegance and poor stability. Shrinkage, which is caused by an inefficient freeze-drying cycle, may be a sign of partial or micro collapse and may result in poor stability of the pegylated interferon upon storage. Liddedness is a physical defect in which the top of the cake forms a thin film or crust, separate from the bulk of the cake. Meltback refers to a common form of cake collapse that is primarily due to incomplete sublimation (change from solid to vapor state) of the formulation. Meltback is associated with a change in the physical form of the pegylated interferon or moisture pocket(s), which may result in instability and depegylation of the pegylated interferon. Preferably, the percentage of these type of cake defects in the lyophilized powder is less than 50%, more preferably less than 10%, still more preferably less than 2%, and most preferably less than 1%.

The use of trehalose in the formulations of the present invention permit aggressive lyophilization conditions to achieve lyophilized powders having the desired low moisture content and minimal cake defects. Loading the glass containers into the lyophilizer may be performed at ambient pressure between −55° C. and 5° C. The loaded containers may be subjected to freezing at ambient pressure for 1 to 4 hrs at a temperature between −55° C. and −40° C., followed by annealing at ambient pressure for 4 to 8 hours at a temperature between −25° C. and −15° C. The frozen solution is dried in two steps under vacuum at a pressure of between 8 and 100 milliTorr (mTorr), preferably between 15 and 30 mTorr. The primary drying step may be performed for 15 to 35 hrs. at a temperature between −30° C. and −15° C. while the secondary drying step may be performed for 5 to 10 hrs. at a temperature starting as low as 0 to 5° C. and ramping up to 40° C. during the drying period. Unloading the glass containers containing the lyophilized powder may be performed at ambient pressure and at room temperature or below.

The invention contemplates that variations of these lyophilization conditions will produce lyophilized powders having the desired characteristics. The skilled artisan can readily design and test alternate lyophilization processes based on considerations known in the art. See, e.g., Tang and Pikal, *Pharmaceutical Research*, 21(2):191-200 (2004)). A preferred lyophilization cycle for preparing a lyophilized pegylated interferon formulation of the present invention is summarized in Table 1 below.

TABLE 1

Preferred lyophilization cycle for lyophilizing pegylated interferon formulations of the invention.

| STEP | CONDITION VALUE |
|---|---|
| LOADING | |
| Temperature (° C.) | 5 |
| Pressure (mTorr) | Ambient |
| FREEZING | |
| Temperature (° C.) | −50 |
| Pressure (mTorr) | Ambient |
| Time (hrs) | 2 |
| ANNEALING | |
| Temperature (° C.) | −20 |
| Pressure (mTorr) | Ambient |
| Time (hrs) | 6 |
| PRIMARY DRYING | |
| Temperature (° C.) | −20 |
| Pressure (mTorr) | 15 |
| Time (hrs) | 25 |
| SECONDARY DRYING | |
| Temperature (° C.) | 5 to 40 |
| Pressure (mTorr) | 15 |
| Time (hrs) | 6 |
| UNLOADING | |
| Temperature (° C.) | 5 |
| Pressure (mTorr) | Ambient |

This preferred lyophilization cycle requires less than 48 hours to complete, including the time required to change the temperature of the chamber between steps as applicable.

Pegylated interferon formulations, which are prepared according to the preceding description, are very stable during storage at room temperature and above. In one embodiment, the amount of unpegylated interferon in the lyophilized powder, after storage at 40° C. for 30 days, is less than 10%, preferably less than 7.5%, and most preferably less than 5%.

Preferred formulations of the invention are lyophilized in a cartridge and consist essentially of $PEG_{12000}$-interferon alpha-2b in an amount of 67.5 µg, 108 µg, 162 µg or 202.5 µg, 80 mg trehalose dihydrate, 1.013 mg dibasic sodium phosphate anhydrous, 1.013 mg monobasic sodium phosphate monohydrate, and 0.0675 mg polysorbate 80. As used herein, the term "consisting essentially of" means that the lyophilized powder contains only the specified materials and other materials that do not materially affect the biological activity or stability of the formulation, and which do not materially affect any specifically claimed properties of the formulation, such as moisture content or amount of cake defects. Particularly preferred formulations consist of the ingredients listed in this paragraph.

The pegylated interferon formulations of the invention are useful in treating diseases or conditions that respond favorably to interferon therapy such as cancer and other cell proliferation disorders, and viral infections. To administer a formulation of the present invention, the lyophilized powder is reconstituted in a sterile diluent, preferably Water for Injection, and then a therapeutically effective amount of the reconstituted formulation is injected into the patient to be treated.

EXAMPLES

Pegylated interferon solutions containing varying amounts of trehalose and sucrose as a cryoprotectant were prepared and lyophilized in glass cartridges under varying conditions and the resulting lyophilized powders were tested for cake defects, moisture content and stability of the pegylated interferon. Table 2 below describes the composition of four of these solutions, which were lyophilized using the lyophilization conditions set forth in Table 1 above.

TABLE 2

| | Solution[a] | | | |
|---|---|---|---|---|
| Ingredient | A | B | C | O |
| $PEG_{12000}$-interferon α-2b | 100-300 µg/ml | 100-300 µg/ml | 100-300 µg/ml | 100-300 µg/ml |
| Sodium phosphate dibasic anhydrous | 1.5 mg/ml | 1.5 mg/ml | 1.5 mg/ml | 1.5 mg/ml |
| Sodium phosphate monobasic monohydrate | 1.5 mg/ml | 1.5 mg/ml | 1.5 mg/ml | 1.5 mg/ml |
| Polysorbate 80 | 0.1 mg/ml | 0.1 mg/ml | 0.1 mg/ml | 0.1 mg/ml |
| Sucrose | 50 mg/ml | 20 mg/ml | 0 mg/ml | 80 mg/ml |
| Trehalose dihydrate | 50 mg/ml | 80 mg/ml | 90 mg/ml | 0 mg/ml |

[a]Each solution was prepared in Water for Injection.

Following lyophilization (using the lyophilization cycle set forth in Table 1), the number of cakes that would normally be rejected due to collapsed cakes, lidded cakes, severely shrunken cakes and meltbacks was determined and the moisture content was measured. The results are shown in Table 3.

TABLE 3

Comparison of % cake rejects for formulations prepared from solutions O, A, B, and C

| Formulation | Trehalose (mg/ml) | Sucrose (mg/ml) | % Cake Rejects | % Moisture |
|---|---|---|---|---|
| O | 0 | 80 | 100 | nd |
| A | 50 | 50 | 100 | nd |
| B | 80 | 20 | 44 | ~3 |
| C | 90 | 0 | 10 | ~2 |

Note:
"nd" means not determined

As evidenced by the data in Table 3, use of trehalose as a cryoprotectant, alone or in combination with sucrose, led to a lower rate of cake rejects due to decreased cake defects (e.g., collapse, shrinkage, liddedness, and meltback).

In addition, the affect of various concentrations of trehalose on the stability of pegylated interferon was assessed by measuring the % of free interferon, which corresponds to the level of depegylation (i.e., hydrolysis), that was present when the lyophilized powder was stored for thirty days at 40° C. The results are shown in Table 4.

TABLE 4

Comparison of % free interferon in lyophilized powders prepared from solutions O and C.

| | % Free Interferon | | |
|---|---|---|---|
| | 90 mg/ml Trehalose Solution C | | Trehalose-free Solution O |
| Time (Days) | 0.5 ml fill | 0.7 ml fill | 0.7 ml fill |
| 0 | 1.96 | 1.91 | nd |
| 1 | 2.22 | 2.21 | nd |
| 5 | 2.83 | 2.9 | nd |
| 14 | 3.53 | 3.7 | nd |
| 21 | 4.18 | 4.03 | nd |
| 30 | nd | 5.19 | 16.5 |

Note:
0.5 ml fill or 0.7 ml fill refers to the amount of the solution lyophilized in a glass cartridge;
"nd" means not determined As evidenced by the data in Table 4, use of trehalose as the cryoprotectant led to decreased depegylation (hydrolysis) of pegylated interferon α-2b in the lyophilized powder.

Various publications are cited herein, the disclosures of which are incorporated by reference in their entireties.

What is claimed:

1. A solution for preparing a lyophilized powder formulation, the solution comprising a pegylated interferon, one or more cryoprotectant agents, a buffer, a stabilizer, and water, wherein trehalose comprises at least 80%, by weight, of the cryoprotectant agents, and the buffer maintains the pH of the formulation between 4.5 and 7.1.

2. The solution of claim 1, wherein one of the cryoprotectant agents is sucrose.

3. The solution of claim 1, wherein trehalose is the sole cryoprotectant agent.

4. The solution of claim 3, which comprises 90 mg/ml trehalose.

5. The solution of claim 1, wherein the buffer maintains the pH of the solution between 6.5 and 7.1.

6. The solution of claim 5, wherein the buffer consists of sodium phosphate dibasic anhydrous and sodium phosphate monobasic monohydrate.

7. The solution of claim 1, wherein the stabilizer is a polysorbate.

8. The solution of claim 7, wherein the polysorbate is polysorbate 80.

9. The solution of claim 1, wherein the pegylated interferon consists of covalent conjugates between PEG molecules and interferon alpha molecules.

10. The solution of claim 9, wherein the PEG molecules are attached to the interferon molecules with a urethane bond.

11. The solution of claim 10, wherein at least 15% of the attached PEG molecules are attached to histidine residues of the interferon alpha molecules.

12. The solution of claim 11, wherein the pegylated interferon alpha is $PEG_{12000}$-interferon alpha-2b.

13. The solution of claim 12, which consists of between 100 and 300 μg/ml of $PEG_{12000}$-interferon alpha-2b, 90 mg/ml trehalose dihydrate, 1.5 mg/ml sodium phosphate dibasic anhydrous, 1.5 mg/ml sodium phosphate monobasic monohydrate, 0.1 mg/ml polysorbate 80 and water.

14. A lyophilized powder, produced by lyophilization of a solution comprising pegylated interferon, one or more cryoprotectant agents, a buffer, a stabilizer, and water, wherein trehalose comprises at least 80%, by weight, of the cryoprotectants agents, the buffer maintains the pH of the solution between 4.5 and 7.1 and the lyophilized powder has a moisture content of less than 3%.

15. The powder of claim 14, which has a moisture content of less than 2%.

16. The powder of claim 15, which has less than 10% unpegylated interferon after storage at 40° C. for 30 days.

17. The powder of claim 15, which is lyophilized in a cartridge.

18. The powder of claim 17, wherein the solution consists essentially of between 100 and 300 μg/ml of $PEG_{12000}$-interferon alpha-2b, 90 mg/ml trehalose dihydrate, 1.5 mg/ml sodium phosphate dibasic anhydrous, 1.5 mg/ml sodium phosphate monobasic monohydrate, 0.1 mg/ml polysorbate 80 and water.

19. The powder of claim 18, wherein the lyophilization is performed using a lyophilization cycle comprising the following steps and condition values:

| STEP | CONDITION VALUE |
|---|---|
| LOADING | |
| Temperature (° C.) | 5 |
| Pressure (mTorr) | Ambient |
| FREEZING | |
| Temperature (° C.) | −50 |
| Pressure (mTorr) | Ambient |
| Time (hrs) | 2 |
| ANNEALING | |
| Temperature (° C.) | −20 |
| Pressure (mTorr) | Ambient |
| Time (hrs) | 6 |
| PRIMARY DRYING | |
| Temperature (° C.) | −20 |
| Pressure (mTorr) | 15 |
| Time (hrs) | 25 |
| SECONDARY DRYING | |
| Temperature (° C.) | 5 to 40 |
| Pressure (mTorr) | 15 |
| Time (hrs) | 6 |
| UNLOADING | |
| Temperature (° C.) | 5 |
| Pressure (mTorr) | Ambient. |

20. A process for preparing a lyophilized pegylated interferon formulation, comprising:

providing a solution which comprises a pegylated interferon, one or more cryoprotectants agents, a buffer, a stabilizer, and water, wherein trehalose comprises at least 80%, by weight, of the cryoprotectant agents and the buffer maintains the pH of the formulation between 4.5 and 7.1;

placing the solution into a glass container; and lyophilizing the solution using a lyophilization cycle that produces a lyophilized powder having a moisture content of less than 3%.

21. The process of claim 20, wherein the glass container is a vial.

22. The process of claim 20, wherein the lyophilization cycle comprises:

loading the glass container into a lyophilizer at ambient pressure and a temperature between −55° C. and 5° C.;

incubating the glass container at ambient pressure for 1 to 4 hrs at a temperature between −55° C. and −40° C. to freeze the solution in the glass container;

incubating the glass container containing the frozen solution at ambient pressure for 4 to 8 hours at a temperature between −25° C. and −15° C. to anneal the pegylated interferon in the solution;

drying the frozen and annealed solution under vacuum at a pressure between 8 and 100 milliTorr (mTorr) using a primary drying step and a secondary drying step, wherein the primary drying step is performed for 15 to 35 hrs. at a temperature between −30° C. and −15° C. and the secondary drying step is performed for 5 to 10 hrs. at a temperature starting at 0° C. to 5° C. and ramping up to 40° C. during the secondary drying period; and unloading the glass container from the lyophilizer at ambient pressure and a temperature of 25° C. or below.

23. The process of claim 22, wherein the glass container is a cartridge and the lyophilization cycle comprises the following steps and condition values:

| STEP | CONDITION VALUE |
| --- | --- |
| LOADING | |
| Temperature (° C.) | 5 |
| Pressure (mTorr) | Ambient |
| FREEZING | |
| Temperature (° C.) | −50 |
| Pressure (mTorr) | Ambient |
| Time (hrs) | 2 |
| ANNEALING | |
| Temperature (° C.) | −20 |
| Pressure (mTorr) | Ambient |
| Time (hrs) | 6 |
| PRIMARY DRYING | |
| Temperature (° C.) | −20 |
| Pressure (mTorr) | 15 |
| Time (hrs) | 25 |
| SECONDARY DRYING | |
| Temperature (° C.) | 5 to 40 |
| Pressure (mTorr) | 15 |
| Time (hrs) | 6 |
| UNLOADING | |
| Temperature (° C.) | 5 |
| Pressure (mTorr) | Ambient. |

24. A pegylated interferon drug product, which comprises a lyophilized powder in a glass container, wherein the lyophilized powder comprises a pegylated interferon, one or more cryoprotectant agents, a buffer, and a stabilizer, wherein trehalose comprises at least 80%, by weight, of the cryoprotectant agents, and the buffer maintains the pH of the formulation between 4.5 and 7.1.

25. The pegylated interferon drug product of claim 24, wherein trehalose is the sole cryoprotectant agent.

26. The pegylated interferon drug product of claim 24, wherein the glass container is a vial.

27. The pegylated interferon drug product of claim 24, wherein the buffer consists of sodium phosphate dibasic anhydrous and sodium phosphate monobasic monohydrate and the stabilizer is a polysorbate.

28. The pegylated interferon drug product of claim 27, wherein the polysorbate is polysorbate 80.

29. The pegylated interferon drug product of claim 27, wherein the pegylated interferon consists of covalent conjugates between PEG molecules and interferon alpha molecules, wherein the PEG molecules are attached to the interferon alpha molecules with a urethane bond.

30. The pegylated interferon drug product of claim 29, wherein at least 15% of the attached PEG molecules are attached to histidine residues of the interferon alpha molecules.

31. The pegylated interferon drug product of claim 30, wherein the glass container is a cartridge having first and second chambers, wherein the lyophilized powder is in the first chamber and the second chamber comprises water.

32. The pegylated interferon drug product of claim 31, wherein the pegylated interferon alpha is $PEG_{12000}$-interferon alpha-2b.

33. The pegylated interferon drug product of claim 32, wherein the lyophilized powder consists essentially of 67.5 μg of $PEG_{12000}$-interferon alpha-2b, 60.780 mg trehalose dihydrate, 1.013 mg dibasic sodium phosphate anhydrous, 1.013 mg monobasic sodium phosphate monohydrate, and 0.0675 mg polysorbate 80.

34. The pegylated interferon drug product of claim 32, wherein the lyophilized powder consists essentially of 108 μg of $PEG_{12000}$-interferon alpha-2b, 60.780mg trehalose dihydrate, 1.013 mg dibasic sodium phosphate anhydrous, 1.013 mg monobasic sodium phosphate monohydrate, and 0.0675 mg polysorbate 80.

35. The pegylated interferon drug product of claim 32, wherein the lyophilized powder consists essentially of 162 μg of $PEG_{12000}$-interferon alpha-2b, 60.780 mg trehalose dihydrate, 1.013 mg dibasic sodium phosphate anhydrous, 1.013 mg monobasic sodium phosphate monohydrate, and 0.0675 mg polysorbate 80.

36. The pegylated interferon drug product of claim 32, wherein the lyophilized powder consists essentially of 202.5 μg of $PEG_{12000}$-interferon alpha-2b, 60.780 mg trehalose dihydrate, 1.013 mg dibasic sodium phosphate anhydrous, 1.013 mg monobasic sodium phosphate monohydrate, and 0.0675 mg polysorbate 80.

* * * * *

UNITED STATES PATENT AND TRADEMARK OFFICE
CERTIFICATE OF CORRECTION

| | | |
|---|---|---|
| PATENT NO. | : 7,632,491 B2 | Page 1 of 1 |
| APPLICATION NO. | : 11/201731 | |
| DATED | : December 15, 2009 | |
| INVENTOR(S) | : Shameem et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 976 days.

Signed and Sealed this

Second Day of November, 2010

David J. Kappos
*Director of the United States Patent and Trademark Office*